US005726059A

United States Patent [19]
Wickens et al.

[11] Patent Number: 5,726,059
[45] Date of Patent: Mar. 10, 1998

[54] PROSTHETIC RNA AND USE THEREOF TO MODIFY RNA EXPRESSION

[75] Inventors: Marvin P. Wickens, Madison, Wis.; Michael D. Sheets, Berkeley, Calif.

[73] Assignee: Wisconsin Alumni Research Foundation, Madison, Wis.

[21] Appl. No.: 467,038

[22] Filed: Jun. 6, 1995

[51] Int. Cl.$^6$ .............................. C12N 5/00; C12N 5/02; C12N 15/00; C07H 21/02
[52] U.S. Cl. ..................... 435/375; 435/69.1; 435/172.3; 536/23.1; 536/24.1; 536/24.5
[58] Field of Search ............................ 435/69.1, 172.3, 435/375; 536/24.1, 24.5, 23.1

[56] References Cited

PUBLICATIONS

Orkin et al., "Report and recommendations of the panel to assess the NIH investment in research on gene therapy", issued by the National Institutes of Health, Dec. 1995.
Beelman, C.A., and R. Parker, "Degradation of mRNA in Eukaryotes," *Cell*, 81: 179–183 (1995).
Bienroth, S., et al., "Assembly of a Processive Messenger RNA Polyadenylation Complex," *EMBO J.*, 12:585–594 (1993).
Fox, C.A., et al., "Poly(A) Addition During Maturation of Frog Oocytes: Distinct Nuclear and Cytoplasmic Activities and Regulation by the Sequence UUUUUAU," *Genes and Dev.*, 3:2151–2162 (1989).
Gebauer, F., et al., "Translational Control by Cytoplasmic PolyAdenylation of c–mos mRNA Is Necessary for Oocyte Maturation in the Mouse," *EMBO J.*, 13:5712–5720 (1994).
Jackson, R.J., and N. Standart, "Do the Poly(A) Tail and 3' Untranslated Region Control mRNA Translation?" *Cell*, 62:15–24 (1990).

Konarska, M.M., et al., "Trans Splicing of mRNA Precursors in Vitro," *Cell*, 42:165–171 (1985).
Richter, J.D., "Translational Control During Early Development," *BioEssays*, 13:179–183 (1991).
Sheets, M.D., et al., "The 3'–Untranslated Regions of c–mos and Cyclin mRNAs Stimulate Translation by Regulating Cytoplasmid Polyadenylation," *Genes and Dev.*, 8:926–938 (1994).
Sheets, M.D., et al., "Polyadenylation of c–mos mRNA as a Control Point in *Xenopus meiotic* Maturation," *Nature*, 374:511–516(1995).
St. Johnston, D., "The Intracellular Localization of Messenger RNAs," *Cell*, 81:161–170 (1995).
Standart, N., and R.J. Jackson, "Regulation of Translation by Specific Protein/mRNA Interactions," *Biochimie*, 76:867–879 (1994).
Wickens, M., "Springtime in the Desert," *Nature*, 363:305–306 (1993).
Wickens, M., "Forward, Backward, How Much, When: Mechanisms of Poly(A) Addition and Removal and Their Role in Early Development," *Dev. Biol.*, 3:399–412 (1992).
Wickens, M., "Introduction: RNA and the Early Embryo," *Dev. Biol.*, 3:363–365 (1992).

*Primary Examiner*—Jasemine C. Chambers
*Assistant Examiner*—Scott D. Priebe
*Attorney, Agent, or Firm*—Quarles & Brady

[57] ABSTRACT

Translation characteristics of an mRNA molecule in a cell can be altered by providing a prosthetic RNA molecule that includes a regulatory sequence element and a sequence element complementary to a portion of the mRNA molecule. Alteration can affect the translation rate, the mRNA stability, or the localization of the mRNA molecule.

13 Claims, 8 Drawing Sheets

PROSTHETIC RNA AND USE THEREOF TO MODIFY RNA EXPRESSION

STATEMENT REGARDING FEDERALLY SPONSORED RESEARCH OR DEVELOPMENT

This invention was made with United States government support awarded by NIH, Project #'s RO1 GM50942 and RO1 GM31892. The United States Government has certain rights in this invention.

FIELD OF THE INVENTION

The present invention relates to control of genetic expression, and more particularly to the regulation of translation of mRNA molecules.

BACKGROUND OF THE INVENTION

Regulation of cytoplasmic RNAs has been examined in animal systems as diverse as insects, rodents and frogs. For example, much effort has been directed to understanding the immediate post-fertilization developmental events. This was initially of interest from a research standpoint, since virtually no nuclear transcription activity takes place at that developmental stage and, as a result, all regulation is at the RNA level. In somatic cells, regulation of mRNAs in the cytoplasm has long been thought to be masked by transcription-related regulation. Recent work has discovered certain general principles of regulation of cytoplasmic mRNAs in a variety of cell types, including somatic cells. As research studies on cytoplasmic and nuclear RNA expression have begun to unravel the mechanics of such regulatory systems, however, the art has recently begun to consider the prospects for therapeutic intervention in diseases shown to have an RNA expression-related pathological component.

In existing expression-regulating strategies, artificial and natural antisense RNAs can be used to control gene expression at multiple levels[14-16], including translation. Typically, antisense RNAs base pair to an RNA target and thereby prevent its function, either by steric interference or by causing the target's destruction.

SUMMARY OF THE INVENTION

The present invention is summarized in that the expression of a polypeptide from an mRNA molecule that includes a translatable gene sequence coding for the polypeptide can be altered or regulated by a prosthetic RNA molecule that includes a regulatory sequence element and a sequence element complementary to a portion of the mRNA molecule, wherein the complementary sequence element is sufficiently long to permit a non-covalent coupling of the mRNA molecule and the prosthetic RNA molecule. The regulatory sequence can control the translation, stability, localization, or any other property of the mRNA. The sequence and hence the prosthetic RNA can act in either the nucleus or cytoplasm.

The invention is also summarized in that a method for regulating expression of an mRNA molecule that encodes a polypeptide in a cell includes the step of providing in the cell a prosthetic RNA molecule that includes a regulatory sequence element and a sequence element complementary to a portion of the mRNA molecule.

The invention is further summarized in that a non-covalently coupled, hybrid RNA molecule includes an mRNA molecule that comprises a translatable gene sequence coding for a polypeptide and a prosthetic RNA molecule that includes a regulatory sequence element and a sequence element complementary to a portion of the mRNA molecule, wherein the mRNA and the prosthetic RNA are not naturally coupled and wherein the expression in a cell of the polypeptide encoded by the chimeric molecule differs significantly from expression in the cell of the polypeptide encoded by the mRNA molecule.

It is an object of the present invention to provide a method for regulating expression of a polypeptide at the RNA level.

It is a feature of the present invention that expression is regulated by a trans-acting prosthetic RNA molecule.

It is another feature of the present invention that expression is altered by regulating mRNA stability, translation rate, localization, or combinations thereof.

Other objects, features, and advantages of the present invention will become apparent upon consideration of the detailed description of the invention, taken in conjunction with the accompanying drawings.

DETAILED DESCRIPTION OF THE INVENTION

Figure 1:
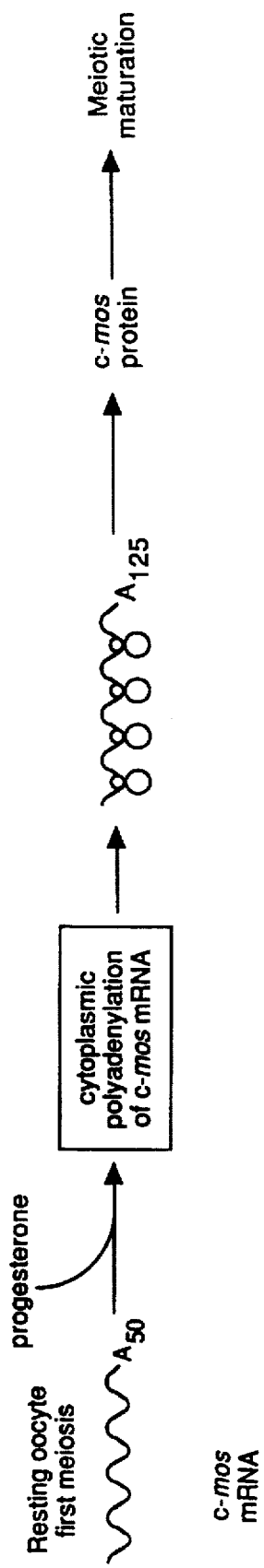
FIG. 1 is a flow chart that depicts the proposed role of cytoplasmic polyadenylation of Xenopus c-mos mRNA in the control of meiosis.

The present invention relates to producing in a target cell a cytoplasmic, hybrid RNA molecule having at least two RNA portions, and to a method for regulating expression by producing such a hybrid molecule. The invention relates to the recognition that certain prosthetic RNA molecules can act in trans in the target cell to alter the expression properties of a target mRNA molecule. Typically, the target mRNA encodes a polypeptide. The encoded polypeptide can be a peptide or protein, as those terms are normally understood in the art. The target mRNA molecule is acted upon by a prosthetic mRNA in the method of the present invention, such that expression from the target mRNA is altered after provision of the prosthetic RNA molecule. The method is a general method for altering expression in the target cell of the target mRNA.

The target cell is the cell in which the hybrid mRNA/ prosthetic RNA forms and in which expression of the encoded polypeptide is altered. Eukaryotic target cells are preferred, although the method can certainly be carried out in prokaryotes. Particular utility in prokaryotes is envisioned in regulating the expression of commercially valuable genes expressed in single cell organisms such as bacteria. In eukaryotes, the target cell can be an animal or plant cell. The preferred eukaryotes are vertebrates, and the most preferred vertebrates are mammals. The target cell can be a gamete, a fertilized egg, or a somatic cell. The accompanying examples describe work in oocytes which are a desirable target cell type is a cell, in that they have a large population of stable mRNA molecules. However, there is no basis for believing that the invention is limited to oocytes or to terminally differentiated cells such as reticulocytes. Rather, it is intended that RNA expression can be regulated in cells of all type in the manner set forth herein.

The structure of a typical target mRNA molecule includes, in addition to the polypeptide-encoding portion, an untranslated region upstream, or 5', to the polypeptide-encoding portion (hereinafter, "5'UTR") and an untranslated portion downstream, or 3', to the polypeptide-encoding portion (hereinafter, 3'UTR"). Whereas the polypeptide-encoding portion of the mRNA includes triplets that uniquely correspond to individual amino acids, the untranslated regions are less constrained during evolution and are known to include numerous regulatory elements that affect mRNA stability, polypeptide translation rate, and mRNA localization. Because of the reduced evolutionary constraints, there is a great deal of variation found in the untranslated portions of mRNA. As a result, the number of sequence elements that have evolved is great.

An extremely active research program is now underway to characterize the many regulatory elements that can reside in 5'- and 3'- UTRs. Research is also underway to examine the effects on translation of changes within the coding portions of mRNA molecule, which are also anticipated to be effective in modifying translation. Attention is directed to recent reviews on the subject, in particular to Standart, N. and R. J. Jackson, "Regulation of Translation by Specific Protein/mRNA Interactions," *Biochimie* 76:867–879 (1994), St. Johnston, D., "The Intracellular Localization of Messenger RNAs," *Cell* 81:161–170 (1995), Beelman, C. A. and R. Parker, "Degradation of mRNA in Eucaryotes," *Cell* 81:179–183 (1995), and Wickens, M. et al., "Translational Control of Developmental Decisions," in Translational Regulation, Cold Spring Harbor Press, N.Y., in press. All of these documents are incorporated herein by reference. From these reviews, it is apparent that attention has focused initially on the regulatory aspects of the 3'UTR, for the sequences contained therein are the least evolutionarily constrained in eukaryotic mRNA molecules. However, similar regulatory sequences have also been uncovered in the 5'UTR and, it is anticipated that more will be found. Among the elements that would be suitable are sequences that control translation, such as those controlling:

cytoplasmic polyadenylation (e.g., c-mos (Sheets, et al., *Nature* 374:511-6 (1995) and Gebauer, F. et al., *EMBO J.* 13:5712–5720 (1994)) and cyclins (Sheets, M. D., Fox, C. A., Hunt, T., Vande Woude, G. & Wickens, M. Genes Der. 8, 926–938 (1994))

masking (Standart, Sem. on Dev. Biol., 3:367–379 (1992) and Standart et al. *Genes and Development*, 4:2157–2168 (1990))

translational repression (e.g., in C. elegans, fem-3 (Ahringer and Kimble, *Nature* 349:346-8 (1991), tra-2 (Goodwin et al., *Cell* 75:329–339 (1993), and lin-14 (Wightman et al., *Cell* 75:855–862); in drosophila, bicoid (Wharton and Struhl, *Cell* 67:955–967 (1991) and nanos (Gayis and Lehmann, *Nature* 369:315-8 (1994); and, in vertebrates, lox-15 (Ostareck-Lederer et al., *EMBO J.* 13:1476-81 (1994))

mRNA stability (e.g., c-fos (Shyu et al., *Genes Dev.* 5:221-34 (1991), c-myc (Brewer, *Mol. Cell. Biol.*, 11:2460-6 (1991), and MFA2 (Decker and Parker *Genes Dev.*, 7:1632-43 (1993))

mRNA localization (e.g., cytoskeletal actin (Lawrence and Singer, *Cell*, 45:407-15 (1986) and bicoid (MacDonald et al., *Development*, 118:1233–1243 (1993)).

Because the art is actively researching the regulatory sequences of many eukaryotic and prokaryotic genes from many organisms, the full catalogue of such elements and the range of activities they possess is not now known. However, the principle of the invention described herein is applicable to any such regulatory element whether it be now known or subsequently revealed.

The target mRNA molecule acted upon by the prosthetic RNA can encode a translatable polypeptide. The mRNA need not encode any particular polypeptide, since the invention affects the mechanism of translation, rather than the structure of the translated polypeptide itself. Moreover, the mRNA need not natively include any particular regulatory sequences, since practice of the invention provides to the mRNA any desired regulatory sequence that alters expression from the mRNA.

The target mRNA molecule to be altered can include the 5' and 3'UTRs and a coding region, or can be a truncated, or amputated, molecule. Truncation in the mRNA 3'UTR is at a site 3' to the polypeptide-encoding portion and 5' to the portion of the native 3'UTR that includes the regulatory sequence. In some cases, amputation prior to adding the prosthetic is preferred, to avoid a situation wherein competing regulatory elements direct the mRNA in competing ways. Amputation eliminates from the molecule the undesired regulatory element or elements.

Elimination of the undesired element puts the mRNA under the exclusive control of the element located on the prosthetic RNA.

In other cases, however, truncation is not needed, as in the case where the endogenous regulatory element is defective or absent and the prosthetic element provides a desired function not otherwise encoded on the mRNA.

Truncation or amputation can be accomplished by providing, in the cell containing the mRNA molecule, an oligonucleotide complementary to a portion of the molecule at which truncation is desired. When the oligonucleotide hybridizes to the mRNA molecule, attack of the double stranded region by RNase H specifically hydrolyzes phosphodiester bonds of RNA hybridized to DNA, producing 3'-OH and 5'-P terminated products. RNase H is a nuclease common to most organisms. Thus, it is be expected that addition of an appropriate oligonucleotide will result in specific amputation as desired. Such an effect is shown in Xenopus in the accompanying examples, but the widespread existence in most organisms of enzymes having activity comparable to RNase H suggests that truncation in vivo is reasonably predicted in other target organisms.

The target mRNA molecule in the cytoplasm of the target cell molecule can be a naturally occurring, intracellular mRNA molecule resident in the target cell, but need not be. The target mRNA can alternatively be provided to the cell from the outside, either as an RNA molecule or as a transcription product of an introduced genetic construct. The delivery of genetic material can be accomplished by any known genetic delivery method, such as microinjection, transfection, transduction, electroporation, particle-mediated gene transfer, or the like. Introduction of genetic material into target cells using particle-mediated gene transfer is described, for example, in U.S. Pat. No. 4,945,050 (Sanford et al.) and U.S. Pat. No. 5,015,580 (Christou et al.), both of which are incorporated herein by reference.

One advantage of practicing the invention on non-native mRNA molecules is that such molecules can have any attribute desired by the genetic engineer. For example, the genetic engineer can produce and deliver, using methods known to the art, a genetic construct that has high or low transcription levels, or that incorporates a particular structural domain into an encoded polypeptide, or that includes particular regulatory segments to facilitate a desired response upon transfer.

Any of these attributes can subsequently be modified as will be described in more detail below using the method of the present invention to, for instance, regulate or alter the expression characteristics of the encoded mRNA any time after delivery. This ability to introduce a gene having particular properties and to subsequently modify those properties as desired suggests strongly the possibility of therapeutic strategies premised upon the recognition that differential expression of certain polypeptides is recognized as a contributing factor to both the induction of a disease state and to its resolution.

The target mRNA can also be a chimeric mPaNA that can result from targeted introduction of a gene, or a portion of a gene, into a gene already present in the target cell. Thus, the mRNA can be a composite transcript encoded in part by a naturally occurring gene and in part by an introduced gene. Recombinant RNA molecules produced in cells using a ribozyme ligase activity are also appropriate target mRNAs.

The target mRNA can be resident in the cell when the prosthetic RNA is added. Alternatively, the two molecules can be provided to the target cell at the same time.

Whatever the mechanism for providing the target mRNA in the cell, it is well within the ability of those skilled in the art to confirm the existence and size of the target mRNA in the target cell by using radioactive or non-radioactive hybridization to complementary nucleic acid probes, or PCR analysis. The same analyses can be used, for example, to determine whether an mRNA has been polyadenylated (if this is the property sought to be regulated).

In the method, expression from the target mRNA is altered by providing in the cell a prosthetic RNA that includes a regulatory sequence element and a sequence element complementary to a portion of target mRNA molecule. The prosthetic RNA can be provided in any of the same ways that the mRNA can be provided.

The regulatory sequence element can be selected from any of the known sequence elements such as those described in the review articles referred to above or any such sequence elements subsequently discovered that perform a regulatory function. The regulatory sequences contemplated by the inventors include those involved in RNA stability, alteration of translation rate, and mRNA localization, as described above. The inventors recognize that as regulation of particular genes in additional cellular systems is examined in detail, numerous such sequences will be identified in addition to those now known, in much the same way as transcriptional regulatory sequences have been elucidated over the years. Any of these sequences are envisioned to work within the principle of the present invention as described herein, because the invention in its broadest form involves providing to the target mRNA molecule in trans a necessary element not otherwise present in the mRNA. Translation alteration need not mean complete activation or inactivation of translation activity. Subtle changes to sequence elements made using the known and established techniques of genetic engineering, can also act to modulate translation activity levels resulting in subtle but effective changes to translation rate, stability, or localization.

The regulatory sequences provided in the prosthetic RNA need not be natively employed as regulatory sequences by the target mRNA or by any natural or native mRNA. In fact, the regulatory sequence of the prosthetic RNA need not derive from a gene in the cell in which the target mRNA occurs. Rather, the regulatory sequences provided by the prosthetic RNA can be obtained from an unrelated gene or from an unrelated cell, or can even be laboratory-engineered, using a known method for producing RNA molecules. Laboratory engineering is the most preferred source of a prosthetic RNA for use in the method, since it permits the user to craft a molecule having desired attributes. Although this is preferred, it is equally suitable to include in the prosthetic molecule one or more natural regulatory sequences isolated from a naturally occurring gene when the behavior of the isolated sequence or sequences is sufficiently well characterized to permit the user to predict the effect of providing the sequence on a prosthetic RNA molecule.

In cases in which the prosthetic RNA is prepared in vitro and then introduced into a cell, the RNA may contain any desirable chemical modifications that can include, without limitation, changes in the phosphodiester backbone (e.g., thiophosphate, methylphosphonate), the ribose (e.g., deoxyribose, 2' position modifications), and the base (e.g., artificial and naturally occurring substituents).

It has also been determined, and is described below, that a desired regulatory sequence element need not be attached to the RNA molecule at its natural location. For instance, the Examples below disclose that enhanced translation of a capped mRNA molecule was demonstrated when a prosthetic RNA comprising at its 5' end a 7-MeGpppG cap, was non-covalently hybridized to the 3'UTR of the mRNA.

The regulatory sequence element may respond to an external stimulant. If such is the case, as is the case in the accompanying examples, the desired translation altering activity can be induced by treating the cell with the external stimulant after the prosthetic RNA has been provided. This provides an additional level of control over the timing of altered expression after the prosthetic RNA has been added.

There should be sufficient complementarity between the complementary sequence element of the prosthetic RNA molecule and the target mRNA molecule to permit non-covalent binding between the two in the cell. The length of the complementary sequence is only somewhat critical, as long as one considers the goal to be maintenance of a stable hybrid molecule. Experience in the art has suggested that one would expect the shortest acceptable length to be about fifteen complementary nucleotides. There is no absolute upper limit to the extent of complementarity. It is desirable, however, that the complementary sequence be as short as is needed to achieve acceptable stability, because as the complementary portions become larger, the likelihood increases that the prosthetic RNA will bind to other, unanticipated mRNA molecules, thereby coordinately altering expression from those additional RNA molecules. To enhance hybrid stability, it may also be possible to provide the prosthetic RNA with more than one region of complementarity, to form, in effect, a bubble structure between the mRNA and the prosthetic RNA.

It is preferred that the complementarity be exact over the entire length of the complementary sequence element, however, it is also possible that in particular circumstances, the nature of the complementary sequence element will be such that less than a perfect match is acceptable. Of course, the likelihood that imperfect complementarity is acceptable increases with the length of the complementary sequence element. In the accompanying examples, a 54 nucleotide portion of the prosthetic RNA was exactly complementary to a portion of the RNA that was regulated. A sequence of this length is shown herein to be suitable. One of ordinary skill desiring to use a complementary sequence element of a different length can readily compare the effectiveness of such a sequence by testing the element in vitro in the described system, wherein the only difference between the prosthetic RNAs would be the length and sequence of the complementary sequence element.

When selecting a sequence complementary to a portion of the target mRNA, it is preferred that the complementary portion of the gene not be otherwise involved in regulating translation, since the effect of having a double stranded portion of the RNA is unpredictable. Accordingly, it may be desirable to test several complementary segments in a prosthetic RNA before determining which is most suitable.

A prosthetic RNA can be designed to have more than one complementary sequence element, such that it could anneal to the target mRNA at more than one site, thereby increasing the stability of the mRNA:prosthetic RNA hybrid. It is also possible both that prosthetic RNA can be annealed to any position on a target mRNA molecule and that multiple prosthetic RNA molecules can be bound to a single target mRNA molecule. Among other things, this would facilitate co-regulation at several sites on the target.

The method step of providing the prosthetic RNA to the cell containing the target mRNA can be carried out in in vitro cell culture, as in the accompanying examples. The method of the invention can also be practiced on whole organisms in vivo, or upon ex vivo cells retrieved from the organism which are subsequently returned to the organism after having been altered in a desirable manner. While the experimental work underlying the invention is described in the examples in the frog oocyte system, it is believed that the method of the present invention is equally applicable to any prokaryotic or eukaryotic cell, including plant cells and animal cells. Frog oocytes are accepted a standard model system for basic genetic functions. Support for the existence of comparable abilities in higher animals is provided by the 1994 work of Gebauer, F. et al., "Translational Control by Cytoplasmic Polyadenylation of C-mos mRNA, is Necessary for Oocyte Maturation in the Mouse," *EMBO J.* 13:5712–5720 (1994). Gebauer et al. found an analogous effect of polyadenylation on C-mos mRNA as in the frog oocyte. The work by Gebauer et al. suggests strongly that the general regulatory mechanisms of translational control are maintained among lower and higher vertebrates.

As an example of ex vivo alteration, translation-alteration according to the present invention could overcome a regulatory deficiency that blocks translation of a protein that could act normally if only it could be translated and secreted from the cell. In this embodiment of the method, the target cells are the cells that are unable to translate the desired protein. The target cells could be retrieved from the organism, whereupon the mRNA could be altered as described herein to overcome the block and to permit translation of the polypeptide where none was previously possible. The unblocked cells could then be returned to the organism whereupon development or maturation could proceed as desired.

The prosthetic RNA can be provided to the cell either by direct delivery of the RNA molecule, or by delivery of a genetic construct engineered to produce a transcript that functions as the prosthetic RNA. The DNA construct comprises a DNA sequence complementary on the coding strand to the desired prosthetic RNA and a transcriptional promoter operable in the target cell operably positioned upstream from the transcript-encoding DNA. The promoter can be any promoter known to be operable in the target cell. In plant cells, the nopaline synthase and cauliflower mosaic virus 30S RNA promoters are commonly used and would be suitable. In animals, many promoters (e.g., an MuLV or CMV promoter), among others, are suitable. Other genetic elements known to affect transcription of an introduced DNA construct in a cell would also be appropriate, but are not essential to such a construct. The construct should be able to maintain itself in the cell after delivery until the prosthetic RNA has been transcribed.

After providing the prosthetic RNA to the cell, no additional method steps are required. The complementary portions of the two RNA molecules will form a non-covalent attachment between the two and, as is demonstrated in the accompanying examples, the hybridized prosthetic RNA acts in trans to alter translation of the mRNA molecule.

The following examples are intended only to be exemplary of, but not limiting on, the invention.

EXAMPLES

One gene system that has been studied extensively in connection with translation-related regulation is the c-mos proto-oncogene which encodes a serine-threonine kinase that has been strongly implicated in the control of vertebrate meiosis and the early embryonic cell cycle[1]. In Xenopus, over-expression of c-mos protein causes precocious meiotic maturation and prevents mitotic cleavage after fertilization[2-3-4]. Female mice lacking a functional c-mos gene display reduced fertility due to parthenogenetic activation of the cell cycle, accompanied by ovarian cysts and teratomas[5,6]. Although aberrant expression of c-mos in somatic cells can cause transformation, c-mos messenger RNA is normally found only in the germ line, and is present in the unfertilized egg. In frogs, translation of c-mos mRNA is essential for progression through meiosis I and extrusion of the first polar body[2,7].

Cytoplasmic poly(A) addition is correlated with the activation of many maternal mRNAs in a broad range of species, and can stimulate translation during oocyte maturation and early development[8-9-10]. It is controlled by specific sequences in the 3' untranslated region (3'UTR). These include the highly conserved sequence AAUAAA, and nearby U-rich sequences that have been designated cytoplasmic polyadenylation elements. (CPEs)[8,10]. Sequence inspection shows that the *Xenopus c-mos* 3'UTR contains such elements[11]. Based on these findings, we proposed that cytoplasmic polyadenylation of c-mos mRNA might stimulate translation of c-mos protein and therefore be critical to the onset of meiosis (FIG. 1)[8,11,12]. Consistent with this view, *Xenopus c-mos* mRNA receives poly(A) during maturation[12]. Moreover, the c-mos 3'UTR, linked to a reporter, stimulates translation in a manner that requires polyadenylation[12].

The c-mos proto-oncogene mRNA includes a coding region that encodes the c-mos protein, an upstream 5'UTR and a downstream 3'UTR. The entire sequence of the Xenopus c-mos mRNA is known and has been published by Sagata, N. et al., *Nature*, 335:519–525 (1988). Particular nucleotide numbers referred to herein are relative to the first nucleotide of the poly(A) tail, identified as +1, the preceding nucleotide being identified as −1, unless otherwise noted.

The following examples demonstrate that polyadenylation of c-mos mRNA is a pivotal step in controlling the initiation of meiosis, and not merely a peripheral manifestation of it. These results establish that a regulatory sequence element of the 3'UTR is involved in signalling polyadenylation and that by providing the regulatory sequence in trans to a c-mos mRNA lacking the sequence, polyadenylation activity can be restored. These results demonstrate a novel therapeutic approach using trans-acting RNA prostheses to affect mRNA expression in vivo.

FIG. 1 depicts the proposed role of cytoplasmic polyadenylation of Xenopus c-mos mRNA in the control of meiosis. Xenopus c-mos mRNA is inefficiently translated in resting oocytes[1,7]. Cytoplasmic polyadenylation of c-mos mRNA, caused by progesterone addition, is proposed[8,11,12] to stimulate c-mos translation, thereby elevating the level of c-mos protein. (Changes in the rate of c-mos proteolysis may also contribute to the rise in c-mos protein levels after progesterone treatment[32].) The accumulation of newly synthesized protein leads to completion of meiotic maturation, including activation of maturation promoting factor (MPF), breakdown of the germinal vesicle or nucleus (GVBD), and the appearance of a white spot at the animal pole of the oocyte. Amputation of 3'UTR prevents maturation If polyadenylation of c-mos mRNA is critical for the onset of maturation (FIG. 1), then oocytes containing c-mos mRNA that cannot be polyadenylated should fail to mature.

To test this prediction, Xenopus oocytes were injected with antisense DNA oligonucleotides complementary to segments of the c-mos 3'UTR that lie 126 or 883 nucleotides upstream of the poly(A) tail. The oligonucleotides were purified by denaturing polyacrylamide gel electrophoresis followed by HPLC. The numerical designations of the injected oligonucleotides indicate the positions relative to the nucleotide to which poly(A) is added; S or A indicates antisense or sense orientation relative to c-mos mRNA:
-883S; 25-mer; position -883 to -859 [SEQ ID NO:1]:
5'-ATCTAGTACAGTATCTCAATGTCCA-3'

883A; 25-mer; position -859 to -883 [SEQ ID NO:2]:
5'-TGGACATTGAGATACTGTACTAGAT-3'

126S; 26-mer; position -126 to -101 [SEQ ID NO:3]:
5'-GCACTGAAAATACAAGCAAGGATATG-3'

126A; 26-mer; position -101 to -126 [SEQ ID NO:4]:
5'-CATATCCTTGCTTGTATTTTCAGTGC-3'

Figure 2A:
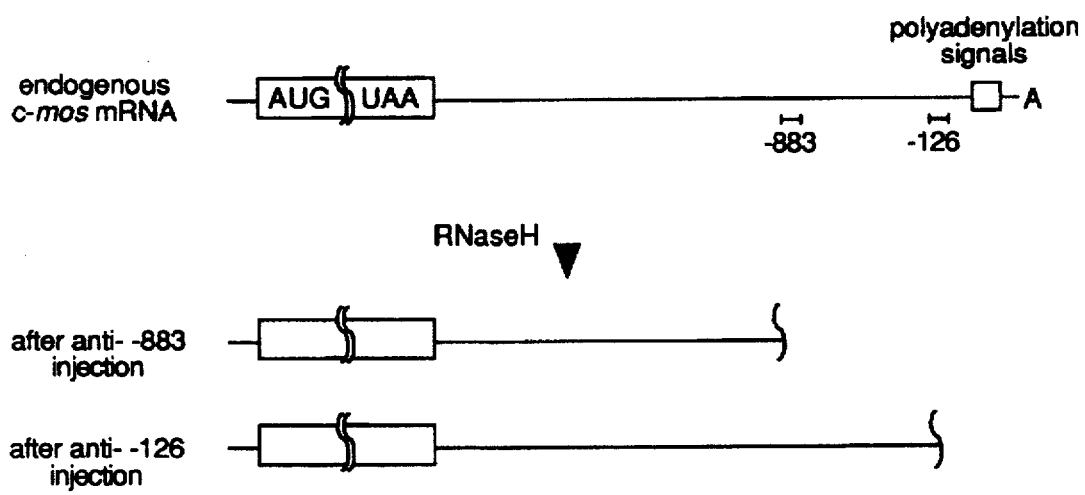
FIG. 2a shows full-length and amputated c-mos mRNA molecules in schematic view.
Figure 2B:
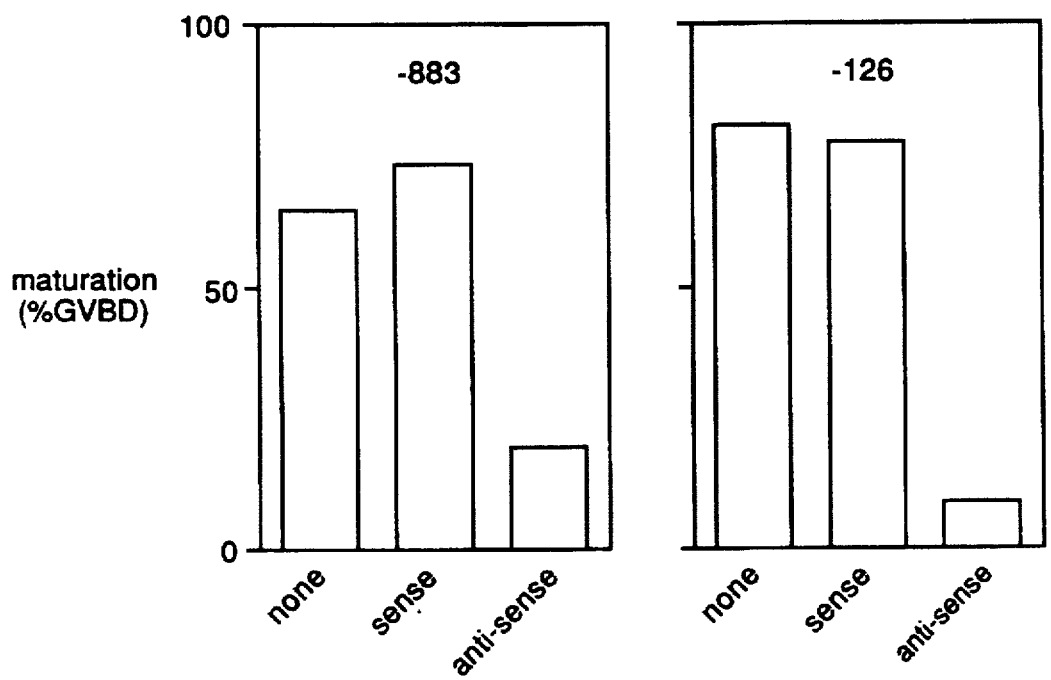
FIG. 2b is a bar chart that shows that amputation of the 3'UTR from the coding region of c-mos mRNA inhibits maturation.

FIG. 2a shows a schematic diagram of c-mos mRNA illustrating the sites to which the antisense oligonucleotides hybridize, relative to the open reading frame (open box), polyadenylation signals (filled box) and poly(A) tail. The polyadenylation signals include both AAUAAA and the CPE. The antisense oligonucleotides anneal to sequences located 126 or 883 nucleotides upstream of the polyadenylation site of c-mos mRNA. FIG. 2a also shows the predicted products resulting from RNaseH digestion after injection of the antisense oligonucleotides into oocytes.

Manually defolliculated oocytes were injected with 100 ng of the sense version or the antisense version of either oligonucleotide, and were then incubated in progesterone (10 μg ml⁻¹). Upon annealing to the mRNA, the antisense oligonucleotides (designated anti-126 and anti-883) caused digestion, as predicted, of the RNA strand of the RNA-DNA duplex by RNaseH present in the oocyte cytoplasm. In this fashion, the polyadenylation signals of c-mos mRNA, including both AAUAAA and the CPE, were severed from the bulk of the mRNA, preventing cytoplasmic polyadenylation (FIG. 2a).

Maturation was scored at a time twice that of $GVBD_{50}$ (defined as the time when half of the oocytes had undergone GVBD), in this and all subsequent experiments, unless noted otherwise. To assay maturation, the appearance of a white spot at the animal pole of the oocyte, indicative of germinal vesicle (nuclear) breakdown (GVBD) and the completion of first meiosis was monitored. In most experiments, absence or presence of a germinal vesicle was checked by fixation in 5% trichloroacetic acid followed by manual dissection. The height of the vertical bar indicates the percentage of the cells that had matured (that is, resumed and completed first meiosis), as assayed by the appearance of white spots at the animal pole. Maturation was assayed blind, without knowledge of how the cells had been treated. The values obtained represent the average of 15 (the -126 oligonucleotides) and 5 (the -883 oligonucleotides) separate experiments. In each experiment, oocytes from a different frog were used and each oligonucleotide was injected into at least 30 oocytes.

Injection of the sense strand of either oligonucleotide sequence has little or no effect on maturation. In contrast, injection of either the anti-126 and anti-883 oligonucleotides inhibits oocyte maturation in response to progesterone. These data have been obtained in 20 experiments, using two different chemical syntheses of the oligonucleotides.

RNAs prepared from oocytes that had been injected with sense or antisense oligonucleotides, and then treated with progesterone, were analyzed by Northern blotting. RNAs were isolated from mature and non-mature cells that were injected with sense or antisense oligonucleotides. RNAs were isolated by homogenization in 50 mM Tris pH 7.9, 5 mM EDTA, 2% SDS and 300 mM NaCl, followed by phenol/chloroform extraction and ethanol precipitation. RNA samples from an equivalent number of cells were denatured with glyoxal and resolved on a 1% agarose gel. Blotting and hybridization were done as described[12]. The RNA hybridization probe was complementary to positions -1,850 to -1,746 of the c-mos 3'UTR, adjacent to the translational termination codon (position -1,951).

Oocytes injected with the sense strand of either oligonucleotide contain full length mRNA. This is true both in the oocytes that did mature in response to progesterone and in those few that did not. In contrast, after injection of either antisense oligonucleotide, oocytes that did not mature contained stable c-mos mRNAs that had been amputated at the 3'UTR by the expected length. The few oocytes that matured in spite of injection of the antisense oligonucleotide contained intact, full-length c-mos mRNA, further reinforcing the conclusion that removal of the end of the c-mos 3'UTR prevents maturation.

Injection of DNA oligonucleotides can have nonspecific effects in oocytes, most notably a general inhibition of protein synthesis.[13] To circumvent this potential complication, each oligonucleotide was purified by a combination of gel electrophoresis and HPLC. As a result, none of the oligonucleotides reduces the level of protein synthesis, as measured either by incorporation of $^{35}S$-methionine into total protein, or by the production of luciferase protein upon co-injection of luciferase mRNA (not shown). Moreover, oocytes injected with antisense oligonucleotides mature in response to low doses of injected c-mos mRNA (see below), attesting to their viability and to the specificity of the inhibition. Thus, the terminal portion of the c-mos 3'UTR is necessary for oocytes to mature in response to progesterone. It controls the translation of the mRNA rather than its stability.

Figure 3A:
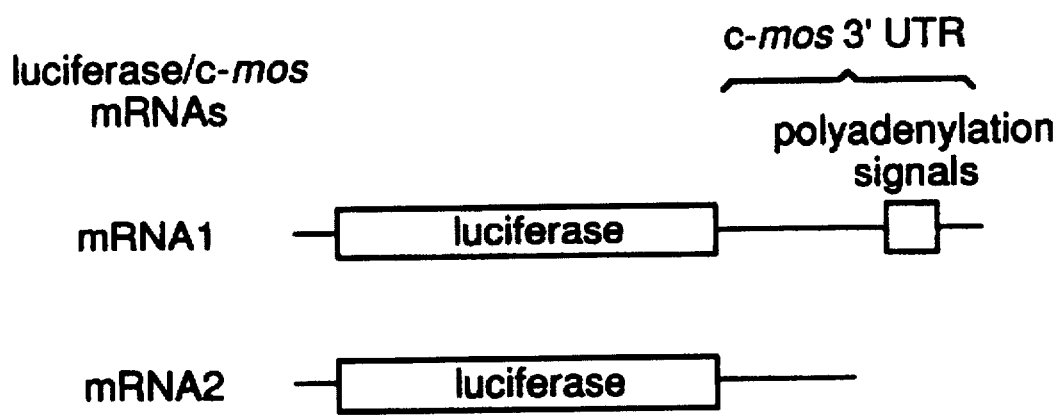
FIG. 3a shows schematic mRNA molecules having or lacking polyadenylation signals.

3'UTR segment stimulates translation c-mos protein appears early in maturation, before $GVBD^{2,7}$. Thus, if the model in FIG. 1 is correct, the c-mos 3'UTR should receive poly(A) and stimulate translation before GVBD. To test this prediction, manually defolliculated oocytes were injected with chimetic mRNAs in which the last 321 nucleotides of the c-mos 3'UTR were joined to a translational reporter, luciferase, the activity of which could be assayed readily. FIG. 3a shows a schematic diagram of the chimeric luciferase/c-mos mRNAs used. mRNA 1 contains 1,680 nucleotides of the luciferase gene followed by the last 321 nucleotides of the wild-type c-mos 3'UTR, including its polyadenylation signals (filled box). The polyadenylation signals include both AAUAAA and a CPE. mRNA 2 is identical, except that it lacks the last 83 nucleotides of the 3'UTR, which contain the polyadenylation signals. mRNAs were prepared by in vitro transcription of the pLuc/c-mos plasmid using T7 RNA polymerase[12], after cleavage with either XhoI (for mRNA 1) or DraI (for mRNA 2). The DraI cleavage site is located 61 nucleotides upstream of the AAUAAA sequence.

Oocytes were injected with 5 ng of the mRNA indicated. Half of the injected cells were incubated in progesterone (10 μg ml$^{-1}$) and the other half were not (−P no progesterone added, +P progesterone added). At various times thereafter, extracts were prepared and luciferase activity measured as described[12].

Figure 3B:
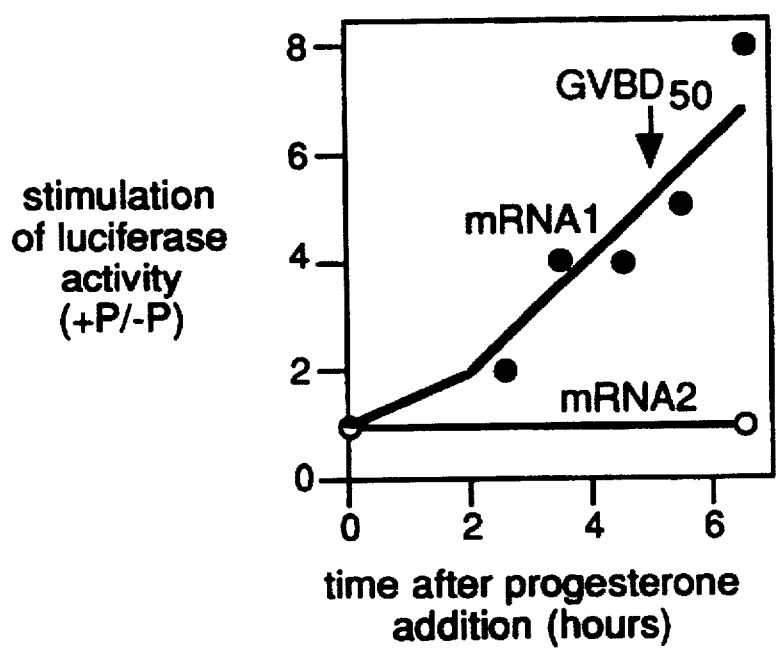
FIG. 3b is a graph that demonstrates that the 3'UTR of c-mos mRNA stimulates translation at or before nuclear breakdown.

Translational activity was assessed at various times after progesterone addition (FIG. 3b). FIG. 3b plots the ratio of luciferase activity present in matured (+P) versus non-matured (−P) oocytes against the time after progesterone addition (Filled circles, mRNA 1; open circles, mRNA 2). GVBD$_{50}$ is indicated by an arrow.

An mRNA carrying a portion of the wild-type 3'UTR, including its polyadenylation signals, stimulated translation four- to fivefold by GVBD$_{50}$ (mRNA 1, FIG. 3), the time when half of the oocytes display a white spot. Translational stimulation was detectable before any oocytes had undergone GVBD. In contrast, translation of an identical mRNA that lacked the last 83 nucleotides of the 3'UTR, including the region removed by the anti-126 oligonucleotide, was not stimulated during maturation (mRNA 2, FIG. 3). Data confirming that wild-type c-mos 3'UTR stimulated translation before GVBD$_{50}$ were obtained from at least 20 oocytes per time point. By injecting mRNAs and analyzing luciferase activity at GVDB$_{50}$, we have obtained similar results in six mRNA 1 and three mRNA 2 experiments. From these results, we conclude that the 3'UTR of c-mos stimulates translation at or before GVBD OCCURS.

Rescue by synthetic c-mos mRNA

Figure 4A:
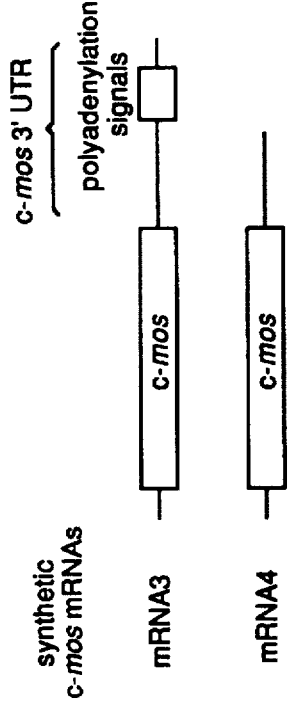
FIG. 4a shows schematic mRNA molecules having or lacking polyadenylation signals.

If oocytes carrying amputated c-mos 3'UTRs fail to mature because they are unable to polyadenylate and translationally activate c-mos mRNA, then their ability to mature should be rescued by injecting c-mos mRNA containing polyadenylation signals. To test this prediction, oocytes that had first been injected with the anti-126 oligonucleotide were subsequently injected with functional c-mos mRNA prepared by transcription in vitro. Schematic diagrams of synthetic c-mos mRNAs with or without c-mos polyadenylation signals are shown in FIG. 4a. mRNA 3 contains the c-mos coding region and 5'UTR joined to the last 83 nucleotides of the c-mos 3'UTR, including its polyadenylation signals, AAUAAA and a CPE (filled box). Synthetic mRNA 3 lacks the region complementary to the antisense DNA oligonucleotide and so cannot be affected by its presence. (In addition, injected oligonucleotides are degraded rapidly in the oocyte cytoplasm.) mRNA 4 is identical to mRNA 3, except that it lacks the last 40 nucleotides of 3'UTR, which contain the polyadenylation signals.

Synthetic c-mos RNAs (mRNAs 3 and 4) were generated from the pGEMc-mos/3'UTR plasmid. pGEMc-mos/3'UTR was constructed by cloning the SacI fragment containing the c-mos coding region from pXmos-8 into the SacI site of pGEM3Z (Promega, Madison, Wis.) to create pGEMXmos-8[2,7]. The 5' end of c-mos cDNA was inserted using synthetic oligonucleotides into the EcoRI and SacII sites of pGEMXmos-8, generating pGEMc-mos[2,7]. The c-mos 3'UTR was added to the coding region by cloning the PstI (blunted with T4 DNA polymerase) XbaI fragment from pGEM-83/+2 c-mos into the BamH1 (blunted with T4 DNA polymerase) XbaI sites of pGEMc-mos, generating pGEMc-mos/3'UTR[12]. This plasmid contains the normal c-mos 5'UTR that begins at the major transcriptional start site (50 nucleotides upstream of the AUG start codon), the natural context of the AUG start codon, the entire c-mos coding region, 203 nucleotides of the c-mos 3'UTR immediately downstream of the translation stop codon followed by the last 83 nucleotides of the c-mos 3'UTR including the signals for maturation-specific poly(A) addition. mRNA 3, containing the c-mos 5'UTR, coding region, and that portion of the 3'UTR present in pGEMc-mos 3'UTR, was transcribed by T7 RNA polymerase from XbaI-cleaved pGEMc-mos/3'UTR[12]. mRNA 4, transcribed by T7 RNA polymerase from NdeI-cleaved pGEMc-mos/3'UTR, is identical except that it ends 41 nucleotides before the poly(A) tail, and so lacks signals required for polyadenylation.

Manually defolliculated oocytes were first injected with 100 ng of the anti-126 oligonucleotide (-126A; bar 3) or with the equivalent sense strand oligonucleotide (-126S; bar 2). After 1 h, oocytes that had been injected with the anti-126 oligonucleotide were injected a second time, with 30 pg of either mRNA 3 or mRNA 4 (bars 4 and 5). Maturation was initiated by adding progesterone (10 μg ml$^{-1}$) to all injected oocytes. As a control, mRNAs 3 and 4 were injected into oocytes that were not subsequently treated with progesterone; neither mRNA induced maturation (bars 6 and 7). The heights of the vertical bars indicate the percentage of the cells that matured, as determined by the appearance of a white spot at the animal pole.

Figure 4B:
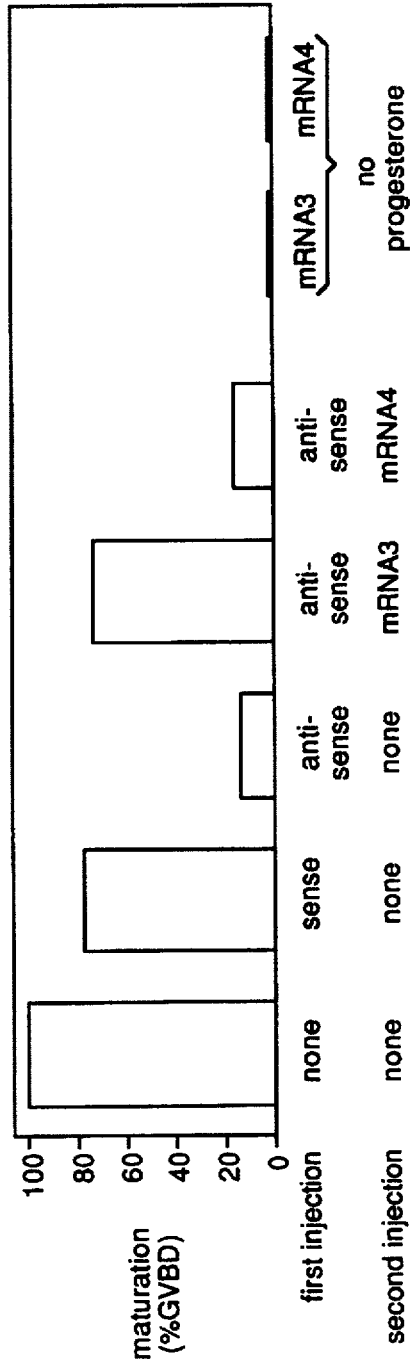
FIG. 4b is a bar chart that shows that oocytes containing truncated c-mos mRNA can mature when provided with a c-mos mRNA containing polyadenylation signals.

As expected, the earlier observation, that oocyte maturation is blocked by adding the antisense nucleotide to amputate the natural mRNA, was confirmed (FIG. 4b). Importantly, the ability of these blocked oocytes to mature in response to progesterone is restored by subsequent injection of the synthetic mRNA 3 carrying polyadenylation signals (See FIG. 4b). Rescue is specific and dependent on polyadenylation signals, as it is much less effective with a mutant c-mos mRNA from which the polyadenylation signals have been deleted (mRNA 4, FIG. 4b).

To test whether the synthetic c-mos mRNAs were capable of maturing oocytes independent of the addition of progesterone, oocytes that had not been injected with any oligonucleotides were injected with 30 pg of either mRNA 3 or mRNA 4. Cells from these injections were not exposed to progesterone. The results represent the average of two separate experiments. In each, oocytes from a different frog were used and each sample was injected into at least 30 oocytes.

Rescue of maturation by synthetic c-mos mRNA was determined to be dose dependent. Manually defolliculated oocytes were first injected with 100 ng of the anti-126 oligonucleotide (-126A). After 1 h, the same oocytes were injected with varying amounts of mRNA 3 (open circles) or mRNA 4 (filled circles). Maturation was initiated by the addition of progesterone of up to 10 μg ml$^{-1}$. The percentage of cells that mature (display a white spot) is plotted against the amount of mRNA in the second injection.

Figure 4C:
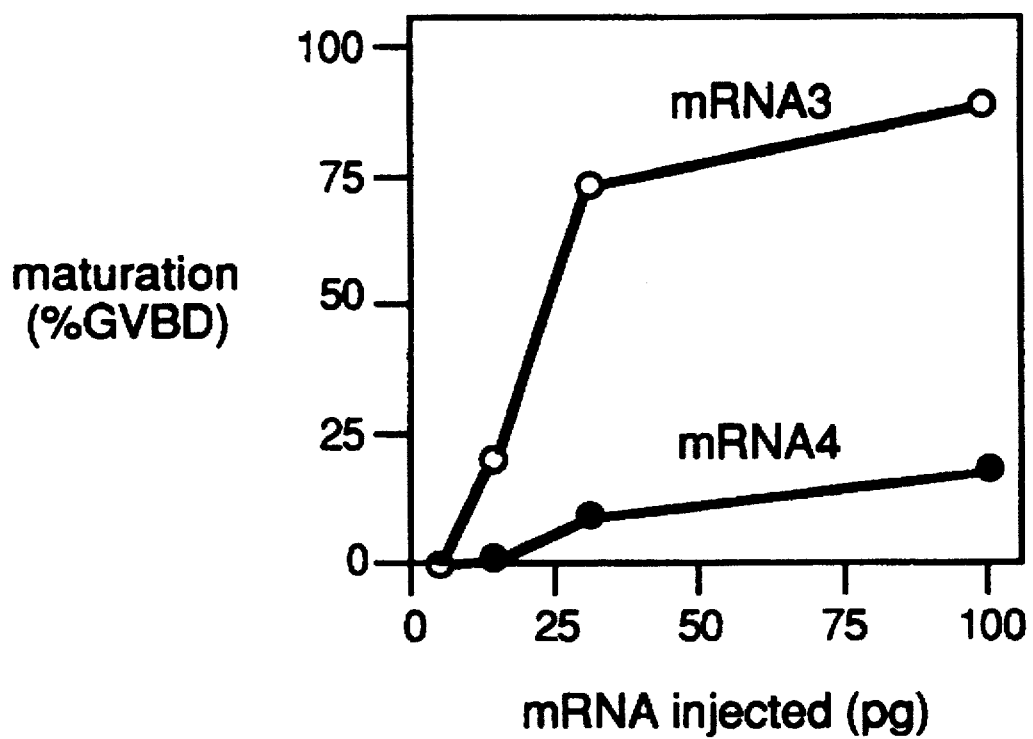
FIG. 4c is a graph that shows a dose dependence for the rescue by c-mos mRNA.

Rescue increased throughout a tenfold range of RNA concentration (FIG. 4c). The mRNA lacking the c-mos polyadenylation signals (mRNA 4) rescues at least tenfold less efficiently than does the mRNA containing them (mRNA 3, FIG. 4c). This is consistent with the observation that the c-mos 3'UTR stimulates translation of a reporter mRNA six- to tenfold (FIG. 3 and ref. 12).

Previous work has demonstrated that injection of large amounts of c-mos mRNA induces maturation even in the absence of progesterone treatment[2]. The mRNA injected in our experiments does not do so (FIG. 4b), presumably because of the dose dependence demonstrated in FIG. 4c; the amount of mRNA injected in our experiments (30 pg) was 100- to 1,000-fold lower than in the earlier work (ref. 2).

Prosthetic RNAs rescue maturation

To test the involvement of c-mos polyadenylation in maturation, we developed a strategy in which a trans-acting RNA, by base pairing to its cellular target, could supply polyadenylation signals and thereby activate the target mRNA translation in trans.

Figure 5A:
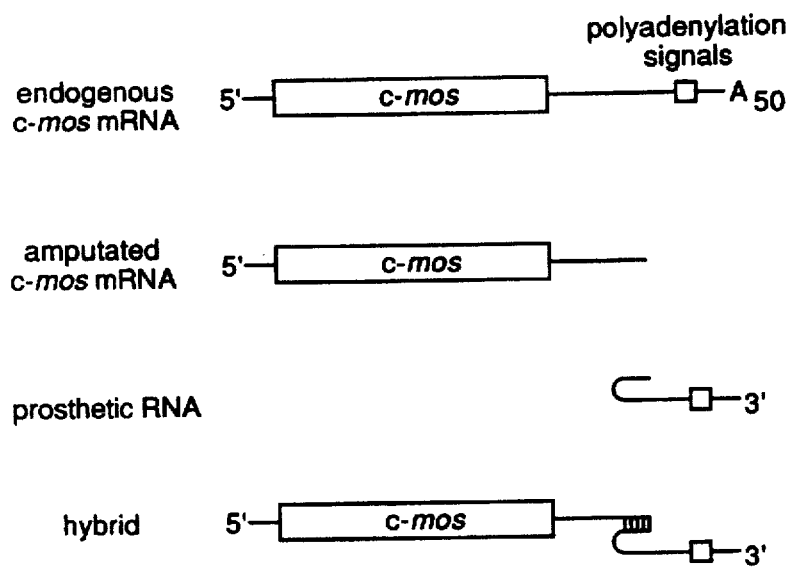
FIG. 5a shows the principle of regulating expression by providing a prosthetic RNA in trans.

The strategy of the experiment is shown in FIG. 5a. Oocytes containing amputated c-mos mRNA, generated as described above, were subsequently injected with a prosthetic RNA designed specifically to reattach polyadenylation signals to the 3' end of amputated endogenous c-mos mRNA, and thereby re-attach polyadenylation signals and rescue its translation activity.

This prosthetic RNA contains, at its 5' end, a sequence complementary to the last 54 nucleotides of c-mos mRNA left after amputation by the anti-126 oligonucleotide, followed by the last 83 nucleotides of the natural c-mos 3'UTR, which included the signals for cytoplasmic polyadenylation and translational activation (FIG. 3). The polyadenylation signals (filled box) include both AAUAAA and a CPE. In addition, the prosthetic RNA contains vector sequences at its 5' end and between the region of complementarity and the 3'UTR sequence. The prosthetic RNA contains a total of 159 nucleotides.

The prosthetic RNA was generated from the plasmid, pGEM/c-mos/prosthetic. An insert containing 54 nucleotides of sequence complementary to positions -196 to -143 of the 3'UTR of the c-mos mRNA was created by annealing two single-stranded DNA oligonucleotides. The region of complementarity was designed to hybridize just upstream of positions -126 to -101 in the 3'UTR of c-mos mRNA, the extreme 3' end of the 3'UTR left after amputation by injection of the antisense oligonucleotide, -126A. The insert containing the region of complementarity was cloned into the HindIII and PstI sites of pGEM-83/+2 c-mos[12] creating pGEM/c-mos/prosthetic. In this plasmid the region of complementarity is positioned upstream of the last 83 nucleotides of the c-mos 3'UTR including the signals necessary for maturation specific poly(A) addition. To generate prosthetic RNA, pGEM/c-mos/prosthetic DNA was cleaved with XbaI and transcribed in vitro using SP6 RNA polymerase and the 5' cap analogue ApppG[11].

If, after annealing to amputated c-mos mRNA, the signals in the prosthetic RNA still cause polyadenylation, then they should cause translational activation. Thus, injection of the prosthetic RNA should enable oocytes containing the amputated mRNA to mature in response to progesterone.

Figure 5B:
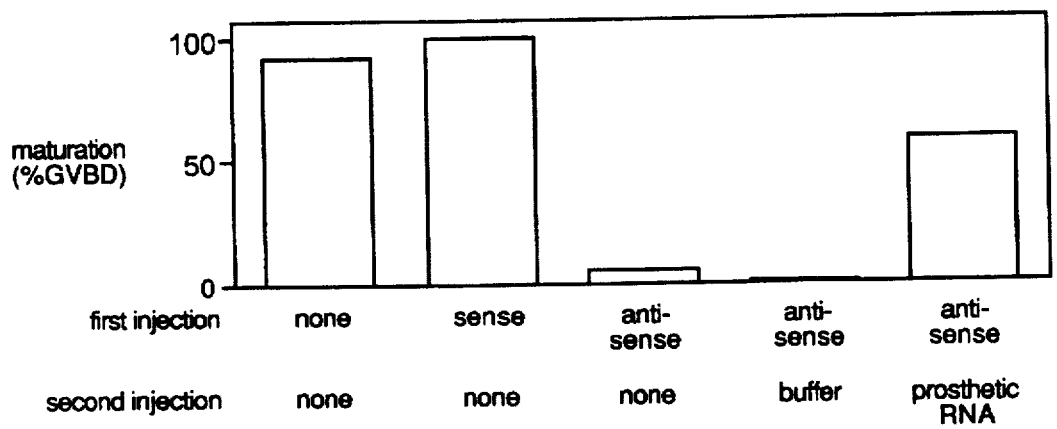
FIG. 5b is a bar chart that demonstrates the rescue of maturation in trans by a prosthetic RNA.

This was, in fact, observed; the prosthetic RNA rescues maturation (FIG. 5b). Manually defolliculated oocytes first were injected with either the antisense oligonucleotide (-126A, bar 3), the equivalent sense strand oligonucleotide (bar 2), or were not injected (bar 1). After 1 h, oocytes that had first been injected with the antisense oligonucleotide received a second injection of either buffer (bar 4) or prosthetic RNA (16 ng; bar 5). Oocytes were then exposed to 10 µg ml$^{-1}$ progesterone and assayed as above. The height of the vertical bar indicates the percentage of the cells that matured (displayed white spots). When oocytes were injected with the anti-126 oligonucleotide, the fraction of oocytes that matured in response to progesterone was reduced to 6%, as compared to 90% without any injection (FIG. 5b). Subsequent injection of the prosthetic RNA rescued maturation, such that 58% of the oocytes injected with the prosthesis matured. Injection of buffer did not rescue maturation.

Complementarity and polyadenylation signals are important for efficient rescue. Injection of variant prosthetic RNAs lacking cytoplasmic polyadenylation signals (FIG. 5c, RNA 1), or lacking complementarity to the amputated c-mos mRNA (FIG. 5c, RNA 2), did not rescue oocyte maturation. Manually defolliculated oocytes were injected with 100 ng of oligonucleotide, either -126S or -126A. A portion of the oocytes injected with -126A were then injected a second time with buffer alone, or with 16 ng of either the prosthetic RNA, RNA 1 or RNA 2. RNA 1 is generated by in vitro transcription with SP6 RNA polymerase of NdeI-cleaved pGEM/c-mos/prosthetic. RNA 1 (118 nucleotides) contains 54 nucleotides complementary to the c-mos 3'UTR followed by 43 nucleotides of the c-mos 3'UTR (nucleotides -83 to -41), but lacking the signals required for maturation-specific poly(A) addition. The remainder of the RNA is composed of vector sequence of the 5' end and between the complementarity and 3'UTR. RNA 2 (referred to elsewhere as -83/+2 c-mos RNA[12]) was generated by in vitro transcription with SP6 RNA polymerase of XbaI-cleaved pGEM-83/+2 c-mos. RNA 2 (113 nucleotides) contains 29 nucleotides of vector sequence followed by 83 nucleotides of the c-mos 3'UTR including its polyadenylation signals (filled box)[11,12]. After injection, maturation was initiated by adding progesterone to the injected cells. All oocytes were exposed to progesterone. The heights of the vertical bars indicate the percentage of the cells that matured.

Restoration of the function of the amputated mRNA, namely the ability of the oocyte to mature in response to progesterone, required that the prosthesis be able to base-pair and carry cytoplasmic polyadenylation signals.

Figure 5C:
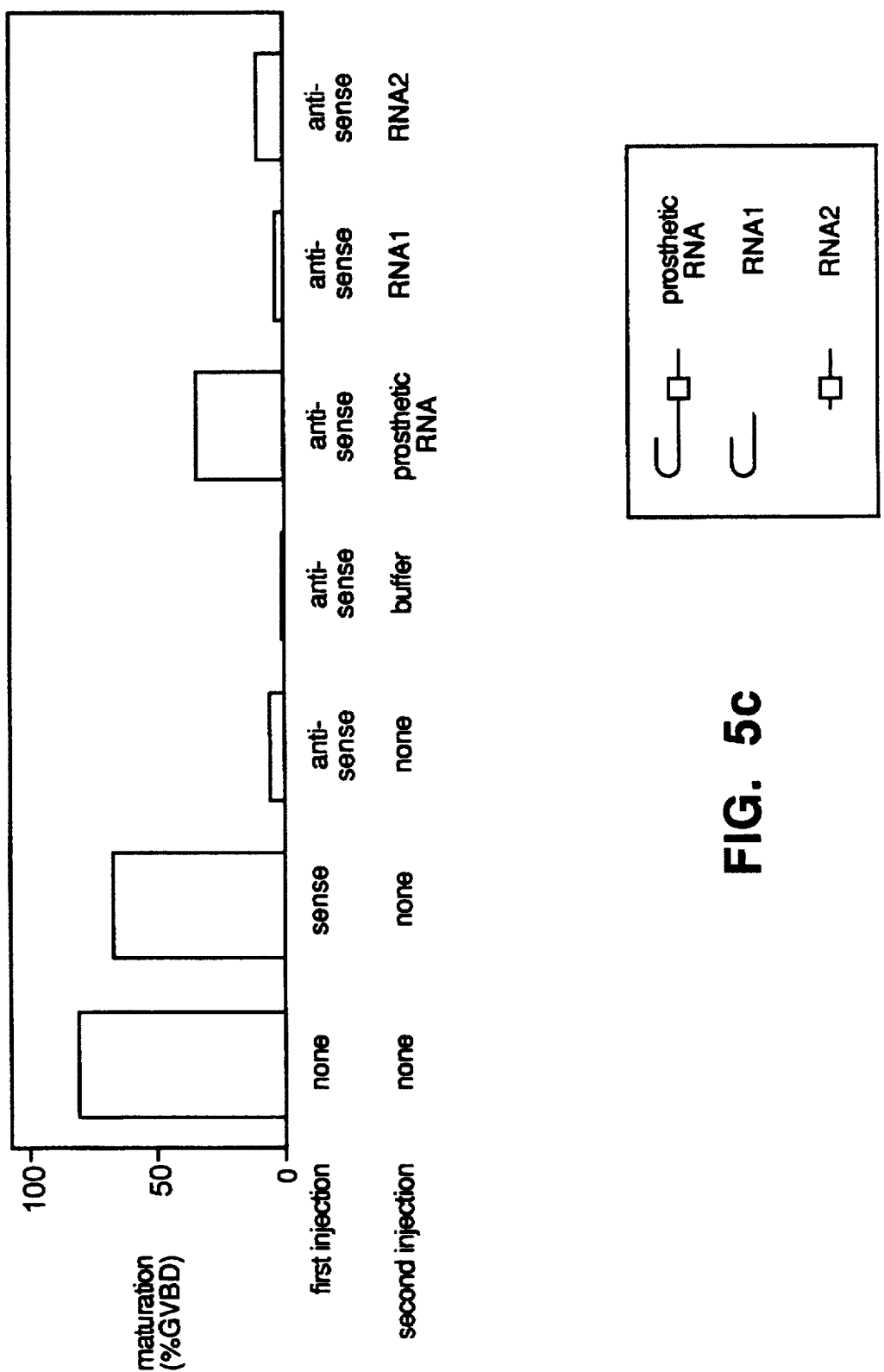
FIG. 5c is a bar chart that shows that rescue by prosthetic RNA requires that the RNA include a complementary sequence element and a expression regulating sequence.

To determine whether the small RNAs received poly(A) during maturation, radiolabeled prosthetic RNAs and variants thereof, as depicted in FIG. 5c, were prepared by transcription in vitro in the presence of $^{32}$P-UTP. Radiolabelled prosthetic RNA, RNA 1 and RNA 2 were generated by in vitro transcription as above[11]. The RNAs were injected into manually defolliculated oocytes and maturation was initiated by adding progesterone (10 µg ml$^{-1}$) to the injected cells. Progesterone-free control cells were also tested. After maturation, RNAs were isolated from injected cells and analyzed by electrophoresis through 8% denaturing polyacrylamide gels[11] followed by autoradiography. RNAs that carried polyadenylation signals received poly(A) during maturation, whether or not they contained sequences complementary to the end of amputated c-mos mRNA. The variant RNA lacking polyadenylation signals was inactive. Rescue by the prosthetic RNA was repeated six times, in experiments using 20 to 30 oocytes per sample. Results with RNA 1 and RNA 2 were obtained twice and once, respectively, in the same experiments. These results demonstrate that polyadenylation signals function in the prosthetic RNAs, and strongly suggest that they can rescue maturation only when attached to c-mos mRNA by base pairing.

The inventors have also shown rescue of oocyte maturation by prosthetic RNA that contained a 5' GpppG cap and the 54 base long complementary sequence. In that trial, the following observations were made. 100% of oocytes matured when no injection was made. Upon injection of an antisense oligonucleotide that can amputate the polyadenylation sequence, only 8% maturation was observed. Yet when the GpppG-capped prosthetic RNA was injected after the amputating polyadenylation sequence, 37% maturation was restored.

Prosthetic RNA stimulates translation

Figure 6A:
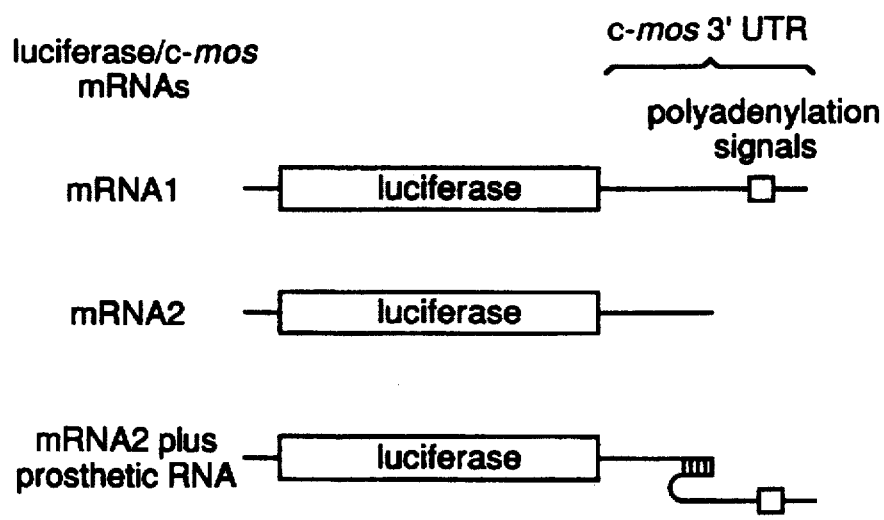
FIG. 6a shows schematic constructs used to test whether prosthetic RNA can rescue translation.

To test directly whether a prosthetic RNA carrying polyadenylation signals stimulates translation (in addition to restoring the capacity to mature), we performed the experiment in FIG. 6. The mRNAs used were the same as in FIG. 3. mRNA 1 contains 1,680 nucleotides of the luciferase gene followed by the last 321 nucleotides of the wild-type c-mos 3'UTR, including its polyadenylation signals (filled box). Polyadenylation signals include both AAUAAA and a CPE. mRNA 2 is identical, except that it lacks the last 83 nucleotides of the 3'UTR, which contain the polyadenylation signals. By design, the 3' end of mRNA 2 is very close to the 3' end of the endogenous c-mos mRNA after it has been amputated by injection of the anti-126 oligonucleotide, -126A. The prosthetic RNA is the same as in FIG. 5. An mRNA was prepared by in vitro transcription that contained a luciferase open reading frame followed by a portion of the c-mos 3'UTR, ending at a similar site to mRNAs that had been amputated with the anti-126 oligonucleotide.

Manually defolliculated oocytes were injected with 5 ng of either mRNA 1, mRNA 2 or mRNA 2 mixed with a threefold molar excess of prosthetic RNA. Half of the injected cells were incubated in progesterone (10 μg ml$^{-1}$) and the other half were not. At the end of maturation (twice GVBD$^{50}$), luciferase activity was measured as described[12]. The experiment was repeated four times with oocytes from different frogs, using 15 to 25 oocytes per point.

Figure 6B:
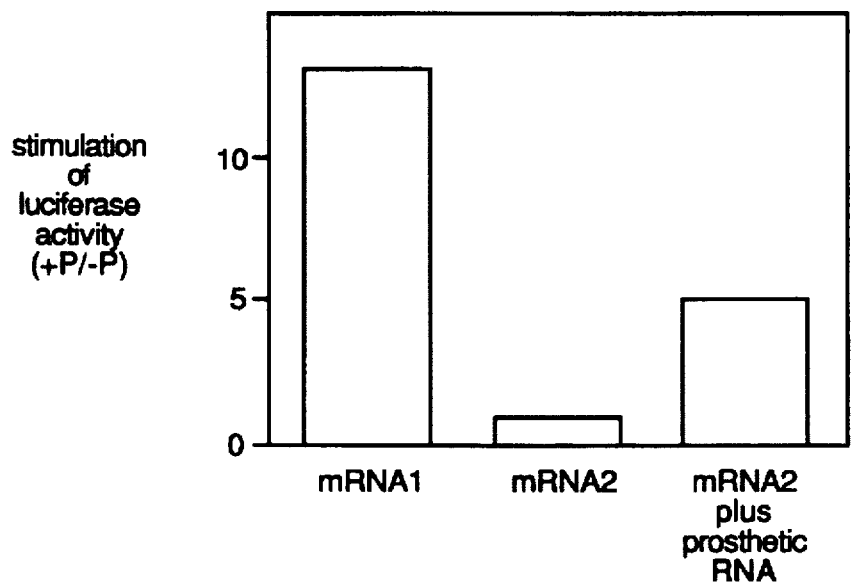
FIG. 6b shows that prosthetic RNA can stimulate translation.

The translation of mRNA 2 after injection, as monitored by luciferase activity, was unaffected by progesterone treatment (FIG. 6b). This was expected because mRNA 2 lacks the signals necessary for polyadenylation during maturation. In contrast, oocytes injected with a mixture of this mRNA and the prosthetic RNA exhibited a fivefold stimulation of translation during oocyte maturation (FIG. 6b). The magnitude of stimulation of mRNA 2 by the prosthetic ranged from three-to sixfold. A representative experiment is shown. An intact mRNA 1, carrying the last 321 nucleotides of the c-mos 3'UTR, including its polyadenylation signals, stimulated translation 13-fold (FIG. 6b). (The level of stimulation seen with mRNA 1 is greater here than in FIG. 3 because the oocytes were incubated for a longer time before assaying luciferase accumulation[12].) The height of the vertical bars indicates the ratio of luciferase activity present in matured (+P) versus non-matured (-P) for each injected sample. From these results we conclude that translation can be stimulated in trans by an RNA carrying cytoplasmic polyadenylation signals.

Polyadenylation as a control point

Our data strongly suggest that polyadenylation of c-mos mRNA is an integral part of the regulatory cascade that initiates meiotic maturation, rather than a secondary consequence of it. c-mos protein is probably required to generate active maturation-promoting factor (MPF), a complex of p34$^{cdc2}$ kinase and cyclin that is critical in cell cycle control[1,33]. If so, it follows that polyadenylation of c-mos mRNA should occur independently of, and before, activation of MPF. The mechanism by which polyadenylation of c-mos mRNA is stimulated may involve activation of a 'core polyadenylation apparatus' that acts on many different mRNAs and contains an RNA binding factor and a cytoplasmic poly(A) polymerase[17-19]. Alternatively, factors that are specific for c-mos mRNA may be activated. Because cytoplasmic polyadenylation also stimulates the translation of cyclin A1, B1 and B2 mRNAs[12], and cyclins are required to form MPF, polyadenylation's involvement in the control of maturation is likely to extend beyond c-mos.

Female mice lacking a functional c-mos gene produce oocytes that complete first meiosis, although more slowly than in wild-type animals[5,6]. This, together with the results reported here and previous work[1,4], implies that the regulation of meiosis differs, at least in part, in mice and Xenopus. As suggested elsewhere[33], as frogs produce large numbers of matured oocytes synchronously and mice do not, there may be different mechanisms of induction in the two species. Consistent with this view, protein synthesis is required for the progression of first meiosis in frogs but not mice[1,20,21]. The translation of c-mos mRNA, stimulated by cytoplasmic polyadenylation, is likely to be one such requisite step. The synthesis of new cyclin proteins[22], which is also likely to be stimulated by cytoplasmic polyadenylation[12], may also be critical.

The experiments reported here identify a biological process in which cytoplasmic polyadenylation probably plays a key regulatory role. Polyadenylation may be a general mechanism used to activate a battery of mRNAs during early development[8]. bicoid mRNA, which is important in establishing the anterior-posterior axis in Drosophila, and fem-3 mRNA, a regulator of sex determination in C. elegans, may be controlled in this fashion, because changes in their poly(A) length are associated with changes in their translational activity[23,24]. Cytoplasmic polyadenylation has been shown to be required for the control of bicoidmRNA translation and pattern formation in Drosophila[30] and of c-mos mRNA translation and meiotic maturation in mice[31].

Trans-acting Prosthetic RNAs

The use of prosthetic RNAs to stimulate translation of an endogenous mRNA suggests new opportunities for intervention into gene expression in vivo. In vitro, previous work demonstrated that two RNAs, by base-pairing, can form competent substrates for splicing[35] and nuclear polyadenylation[36]. Unlike most previously described antisense RNA strategies used in vivo, the prosthetic RNA approach is not limited to inhibition of normal mRNA function. In principle, new activities may be imposed on natural mRNAs in vivo, in animal cells. As with all experiments that require formation of RNA-RNA duplexes in vivo, enzymes that destabilize or degrade RNA duplexes present potential complications. For example, many cells, including frog oocytes, contain an activity (dsRAD) that converts adenosines in double-stranded RNA to inosines, destabilizing the duplexes[25-26]. This activity is nuclear in frog oocytes (as in most cells examined)[27], and so presumably does not interfere with the cytoplasmic RNA duplexes formed in our studies until after nuclear breakdown, by which time c-mos translation has presumably already been activated.

In our experiments, the prosthetic RNA stimulates translation in trans by virtue of its polyadenylation signals. In the same way, other signals might be supplied that would control, for example, the location of the mRNA within the cell, or its stability. Signals that are normally present in the 3'UTR, which have now been discovered in a wide range of mRNAs and animal species[9-28-29-34], are ideal candidates to be supplied in trans. A priori, the target mRNA need only have its 3'UTR or other site available for base pairing to the prosthesis.

The present invention finds particular utility in female animals and humans in overcoming developmental or other problems in eggs. For example, an egg defective in 3'UTR regulation of a specific mRNA (such as c-mos or cyclin) could be rescued through the addition of a prosthetic RNA that restored proper regulation. This rescue could be performed in vitro after removal of the eggs from the animal or human patient in a fertility clinic.

The present invention is not intended to be limited to the embodiments described in the Examples, but rather to encompass all such variations and modifications as come within the scope of the appended claims.

References Cited

1. Yew, N., Strobel, M. & Vande Woude, G. F. *Curr. Opin. Gen. Dev.* 3, 19–25 (1993).

2. Sagata, N., Daar, I., Oskarsson, M., Showalter, S. D. & Vande Woude, G. F. *Science* 245, 643–646 (1989).

3. Freeman, R.S. *Proc. Natl. Acad. Sci. U.S.A.* 86, 5805–5809 (1989).

4. Yew, N., Mellini, M. L. & Vande Woude, G. F. *Nature* 355, 649–652 (1992).

5. Colledge, W. H., Carlton, M. B. L., Udy, G. B. & Evans, M. J. *Nature* 370 65–68 (1994).

6. Hashimoto, N., et al. *Nature* 370 68–71 (1994).

7. Sagata, N., Oskarsson, M., Copeland, T., Brumbaugh, J. & Vande Woude, G. F. *Nature* 333, 519–525 (1988).

8. Wickens, M. *Semin Devl Biol.* 3, 399–412 (1992).

9. Jackson, R. & Standart, N. *Cell* 62, 15–24 (1990).

10. Richter, J. *Bioessays* 13, 179–183 (1991).

11. Fox, C. A., Sheets, M. D. & Wickens, M. P. *Genes Dev.* 3, 2151–2162 (1989).

12. Sheets, M. D., Fox, C. A., Hunt, T., Vande Woude, G. & Wickens, M. *Genes Dev.* 8, 926–938 (1994).

13. Smith, R. C., et al. *Development* 110, 769–779 (1990).

14. Takayama, K. & Inouye, M. *CRC Crit. Rev. Biochem,* 5, 155–184 (1990).

15. Nellen, W. & Lichtenstein, C. *Trends Biochem. Sci.* 18, 419–423 (1993).

16. Simons, R. W. & Kleckner, N. A. *Rev. Genet.* 22, 567–600 (1988).

17. Bilger, A., Fox, C. A., Wahle, E. & Wickens, M. *Genes Dev.* 8, 1106–1116 (1994).

18. Fox, C. A., Sheets, M., Wahle, E. & Wickens, M. *EMBO J.* 11, 5021–5032 (1992).

19. Ballantyne, S., Bilger, A., Astrom, J., Virtanen, A. & Wickens, M. *RNA* (in the press).

20. Mallet, J. L. in *Oogenesis* Vol. 1 (ed. Browder, L. W.) 289–311 (Plenum, New York, 1985).

21. Bachvarova, R. in *Oogenesis* Vol. 1 (ed. Browder, L. W.) 453–524 (Plenum, New York, 1985).

22. Kobayashi, H. et al. *J. Cell Biol.* 114, 755–765 (1991).

23. Wharton, R. & Struhl, G. *Cell* 67, 955–967 (1991).

24. Ahringer, J. & Kimble, J. *Nature* 349, 346–348 (1991).

25. Bass, B. & Weintraub, H. *Cell* 55, 1089–1098 (1988).

26. Wagner, R. W., Smith, J. E., Cooperman, B. S. & Nishikura, K. *Proc. Natl. Acad. Sci. U.S.A.* 86, 2647–2651 (1989).

27. Bass, B. L. *Semin. Devl Biol.* 3.425–433 (1992).

28. Wickens, M. (ed.) Semin. Devl Biol. 3, 363–424 (1992).

29. Wickens, M. *Nature* 363, 305–306 (1993).

30. Salles, F. J., Lieberfarb, M. E., Wreden, C., Gergen, J. P. & Strickland, S. *Science* 266, 1996–1998 (1994).

31. Gebauer, F., Xu, M., Cooper, G. M. & Richter, J. D. *EMBO J.* 13, 5712–5720 (1994).

32. Nishizawa, M., Okazaki, K., Furuno, N., Watanabe, N. & Sagata, N. *EMBO J.* 11, 2433–2446 (1992).

33. Vande Woude, G. F. *Nature* 370, 20–21 (1994).

34. Standart, N. & Jackson, R. *Biochimie* 76, 867–879 (1994).

35. Konarska, M. M., Padgett, R. A. & Sharp, P. A. *Cell* 42, 165–171 (1985).

36. Bienroth, S., Keller, W. & Wahle, E. *EMBO J.* 12, 585–594 (1993).

---

We claim:

1. A method for altering translation in a Cell of an mRNA molecule that comprises a polypeptide-encoding portion, the method comprising the step of:

introducing into a cell cultured in vitro a prosthetic RNA molecule comprising a translation-regulating sequence element and a sequence element complementary to a portion of the mRNA molecule, wherein the translation-regulating sequence element is selected from the group consisting of a polyadenylation element, a mRNA localization element, and a 5' GpppG cap, whereby the stability, localization or translation rate of the mRNA molecule is altered relative to that of the mRNA molecule in the absence of said prosthetic RNA molecule.

2. The method of claim 1 wherein the introducing step comprises the step of:

delivering the prosthetic RNA molecule directly into the cell.

3. The method of claim 1 wherein the introducing step comprises the step of:

delivering into the cell a DNA construct comprising a transcriptional promoter operably joined to a DNA sequence encoding the prosthetic RNA.

4. The method of claim 1 wherein the translation-regulating sequence element responds to an external stimulant and wherein the method further comprises the step of:

treating the cell to which the prosthetic RNA molecule was provided with the external stimulant.

5. The method of claim 1 further comprising the step of:

truncating the mRNA at a position 3' to the polypeptide-encoding portion before providing the prosthetic RNA.

6. The method of claim 5 wherein the cell contains an enzyme that hydrolyzes phosphodiester bonds of RNA/DNA hybrids, the truncating step comprising the step of:

delivering into the cell an antisense oligonucleotide complementary to a portion of the mRNA located 3' to the polypeptide-encoding portion.

7. A non-naturally occurring hybrid molecule comprising:

an mRNA molecule comprising a translatable gene sequence coding for a polypeptide; and a prosthetic RNA molecule comprising a translation-regulating sequence element and a sequence element complementary to a portion of the mRNA molecule, the prosthetic RNA molecule being non-covalently coupled to the mRNA molecule, the translation-regulating sequence element being selected from a group consisting of a polyadenylation element, an mRNA localization element, and a 5' GpppG cap.

8. The hybrid molecule of claim 7 wherein the complementary sequence element of the prosthetic RNA molecule comprises at least 15 consecutive nucleotides complementary to the mRNA molecule.

9. The hybrid molecule of claim 7 wherein the prosthetic RNA molecule comprises a 3' untranslated region of an mRNA.

10. The hybrid molecule of claim 7 wherein the translation-regulating sequence element is a sequence that responds to external regulation.

11. The hybrid molecule of claim 10 wherein the translation-regulating sequence element responds to a hormone.

12. The hybrid molecule of claim 7 wherein the translation-regulating sequence element is a polyadenylation sequence.

13. The hybrid molecule of claim 7 wherein the translation-regulating sequence element is a sequence that alters mRNA localization.

\* \* \* \* \*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide -883S; same sense as c- mos mRNA from positions -883 to -859"

( i i i ) HYPOTHETICAL: NO ( i v ) ANTI-SENSE: NO ( v i ) ORIGINAL SOURCE:

( A ) ORGANISM: Xenopus laevis
            ( G ) CELL TYPE: Oocyte ( x i ) SEQUENCE DESCRIPTION: SEQ ID NO:1:

ATCTAGTACA GTATCTCAAT GTCCA                                                            25

( 2 ) INFORMATION FOR SEQ ID NO:2:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "Oligonucleotide -883A;
                antisense orientation to c-mos mRNA from positions
                - 859 to -883"

( i i i ) HYPOTHETICAL: NO ( i v ) ANTI-SENSE: YES ( v i ) ORIGINAL SOURCE:
            ( A ) ORGANISM: Xenopus laevis
            ( G ) CELL TYPE: Oocyte ( x i ) SEQUENCE DESCRIPTION: SEQ ID NO:2:

TGGACATTGA GATACTGTAC TAGAT                                                            25

( 2 ) INFORMATION FOR SEQ ID NO:3:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "Oligonucleotide -126S; same
                orientation as c-mos mRNA from positions -126 to -101"

( i i i ) HYPOTHETICAL: NO ( i v ) ANTI-SENSE: NO ( v i ) ORIGINAL SOURCE:
            ( A ) ORGANISM: Xenopus laevis
            ( G ) CELL TYPE: Oocyte ( x i ) SEQUENCE DESCRIPTION: SEQ ID NO:3:

GCACTGAAAA TACAAGCAAG GATATG                                                           26

( 2 ) INFORMATION FOR SEQ ID NO:4:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "Oligonucleotide -126A;
                antisense orientation to c-mos mRNA from positions
                - 101 to -126"

( i i i ) HYPOTHETICAL: NO ( i v ) ANTI-SENSE: YES ( v i ) ORIGINAL SOURCE:
            ( A ) ORGANISM: Xenopus laevis
            ( G ) CELL TYPE: Oocyte ( x i ) SEQUENCE DESCRIPTION: SEQ ID NO:4:

```
CATATCCTTG CTTGTATTTT CAGTGC                                    26
```